United States Patent [19]

Lleonart Aliberas

[11] Patent Number: 5,545,561
[45] Date of Patent: Aug. 13, 1996

[54] CONTRAST CHAMBER FOR SPOTLIGHTING BACTERIAL COLONIES WITH RESPECT TO THE CULTURE MEDIUM THEREOF

[75] Inventor: Miguel Lleonart Aliberas, Barcelona, Spain

[73] Assignee: IUL, S.A., Barcelona, Spain

[21] Appl. No.: 252,581

[22] Filed: Apr. 25, 1994

Related U.S. Application Data

[63] Continuation of PCT/ES93/00072, Aug. 27, 1993.

[30] Foreign Application Priority Data

| Aug. 27, 1992 | [ES] | Spain | 9201779 |
| Feb. 3, 1993 | [ES] | Spain | 9300196 |
| Jun. 7, 1993 | [ES] | Spain | 9301241 |

[51] Int. Cl.$^6$ .................. C12M 1/00; C12M 1/34; C12M 1/16
[52] U.S. Cl. .................. 439/287.3; 359/389; 359/479; 359/577; 359/578; 359/584; 359/599; 359/370; 359/368; 211/59.4; 211/188; 211/153; 211/49.1; 211/52; 435/288.3; 435/288.7
[58] Field of Search .................. 211/59.4, 188, 211/153, 49.1, 52; 435/287, 297, 299, 291; 359/389, 479, 577, 578, 584, 599, 370, 368

[56] References Cited

U.S. PATENT DOCUMENTS

| 3,712,746 | 1/1973 | Bergeron | 356/250 |
| 3,736,432 | 5/1973 | Sweet | 377/10 |
| 3,776,817 | 12/1973 | Von Der Pfordten | 435/33 |
| 3,811,036 | 5/1974 | Perry | 377/10 |
| 3,822,941 | 7/1974 | Roche | 356/100 |
| 4,535,239 | 8/1985 | Brighton | 250/340 |
| 4,540,887 | 9/1985 | Minerd et al. | 250/561 |
| 4,665,036 | 5/1987 | Dedden et al. | 435/301 |
| 5,206,171 | 4/1993 | Dillon | 435/30 |
| 5,253,767 | 10/1993 | Koeppel | 211/188 |
| 5,260,826 | 11/1993 | Wu | 359/368 |
| 5,262,840 | 11/1993 | Stearns | 356/334 |

FOREIGN PATENT DOCUMENTS

| 242114 | 10/1987 | European Pat. Off. . |
| 525948A3 | 2/1993 | European Pat. Off. . |
| WO92/12233 | 7/1992 | WIPO . |

OTHER PUBLICATIONS

Messtechnik—vol. 77, No. 6, Jun. 1969—"Auswertung Des Entwickelten Bildes. Messung Der Optischen Dichte (Schärzung) Densitometer".

*Primary Examiner*—Donald E. Czaja
*Assistant Examiner*—Jane Williams Elkin
*Attorney, Agent, or Firm*—Darby & Darby, P.C.

[57] ABSTRACT

The contrast chamber for spotlighting bacterial colonies with respecto to their culture medium performs the automatic counting, through the use of an automatic processor connected to a reading head (7), of bacterial colonies which develop in the capsules wherein the culture takes place; additionally, it also provides for the automatic introduction of the capsules (5) inside the contrast chamber The contrast chamber is provided with lateral lighting means, using the light reflected by a reflection tube (2) and emitted by a lighting source (1) postioned above the capsule (5) which has been closed by a lid provided with an opaque disc (3). The reading head (7) is positioned under the capsule (5) and is associated to a second light source (8) which moves together with the reading head and which is inclined with respect to the surface of the capsule (5), so that the light beams do not impinge on the reading head (7). In the proximity of the contrast chamber there ae provided means (12) for housing in ordered arrangement a plurality of capsules (5) in order to improve the handling and automatic introduction os said capsules (5) into the contrast chamber.

15 Claims, 5 Drawing Sheets

CONTRAST CHAMBER FOR SPOTLIGHTING BACTERIAL COLONIES WITH RESPECT TO THE CULTURE MEDIUM THEREOF

This is a continuation of International application Ser. No. PCT/ES93/00072, filed Aug. 27, 1993.

OBJECT OF THE INVENTION

As is expressed in the title of this specification, the present invention consists of a contrast chamber to spotlight bacterial colonies with regard to the culture medium of the same; whose purpose is to furnish the automatic count by means of an automatic processor, of the bacterial colonies that are grown in the dishes where the culture is made. Another purpose of the invention consists of permitting the automatic introduction of a plurality of dishes in the contrast chamber.

The arrangement, number and form of the bacterial colonies grown after the culture is easily appreciable, upon making the contrast, it being possible to use an electronic image pickup, such as a scanner or other device or optical camera that can carry out the final operation of reading and transcribing the image from the dish to the automatic processor to determine the number of bacterial colonies grown, and to show the image obtained on a screen where the bacteria appear represented in a bright color, so that the visual verification of the count of the same is provided.

BACKGROUND OF THE INVENTION

The practice of making bacterial cultures to determine the number of type of bacteria present in food, pharmaceutical products, etc. is conventionally known.

Now then, the bacterial culture medium is made in some dishes that are known as Petri dishes in which a base product that consists of a gelled agar-agar solution that constitutes food for the bacteria is placed, upon which an extract of the product to be analyzed is placed.

Subsequently the dish is placed in an oven to favor the reproduction of the bacteria, creating different colonies from each microorganism present in the extract of the product to be analyzed.

The problem that arises afterwards consists of making the count of colonies created, in order to establish the amount of bacteria that was contained in the analyzed product.

Conventionally the count is made visually directly or by means of a magnifying glass, which makes it a task that requires a great visual effort and a great deal of concentration, thus, the probability that errors are made in the counts made is considerable, a probability that increases when the operator has to make the count of countless bacterial cultures, since this operation really tires out the person who has to carry it out.

Besides, automatic counting apparatus of bacterial colonies that are based on illuminating the dish and on detecting the image of the same, by means of a video camera, exist. These devices have the problem that multiple reflections are created since the base product coagulates, on occasions, very rapidly and the surface thereof has waves, aside from the bubbles that may appear in the base product, as well as the reflections that the walls themselves of the dish, base and cover thereof create; therefore, it is necessary to remove the cover from the dish to make the count of the bacterial colonies, with the subsequent risk of contamination, that this operation involves, for the user as well as for the culture, aside from the bad smells that are given off upon opening the dish.

Another problem that these devices have consists of the fact that the handling of the dishes is totally manual which makes the process more expensive and hampers the carrying out of the same.

Besides, the dishes are arranged inside the oven, in stacks, the bases contacting with each other, therefore the thermal balance is not attained at the most suitable speed to achieve homogeneous reproduction of colonies in all of the dishes.

DESCRIPTION OF THE INVENTION

In order to solve each and every one of the above cited problems, the invention consists of a contrast chamber to highlight bacterial colonies with regard to the culture medium base of the same that allows the automatic count of the bacterial colonies grown in the culture to be made, without having to remove the covers from the dishes in which the culture is made, and with a minimum probability of error.

Besides, by means of the invention the automatic introduction of the dishes inside the contrast chamber is furnished, simplying the counting process.

In order to achieve these aims, lateral lighting of the dish directly or indirectly is done as it will be explained hereinafter.

In order to furnish indirect lighting, the invention has a reflection tube inside of which there is a lamp that gives off light, which is reflected through the reflection tube.

Inside the reflection tube the Petri dish that remains covered over by a dark shaded opaque disk is placed, so that upon the light from the lamp being given off, the dish is lighted up from all sides, by the reflection of light produced on the inside walls of the tube.

In this situation the light transmitted through the medium, completely lights up the dish the bacterial colonies remaining highlighted upon the dark bottom of the opaque disk.

In order to carry out the direct lateral lighting of the dish, a series of lamps that directly light up the dish is placed lateral to the dish, whereby the bacterial colonies, likewise remain highlighted with regard to the base.

In this way, it is possible to pick up the image of the culture, by means of a reading head, that moves underneath the dish, which is kept closed by its cover and covered on top by a dark opaque disk, without the need of removing the cover to permit the automatic count of the bacterial colonies grown during the culture to be made.

The image can be transmitted to a computer to be processed and shown on a graphic screen, thus carrying out the automatic count and/or visual verification.

This problem is overcome by means of a second light source that is placed over the reading head, slanted enough with regard to the surface of the dish, so that the rays that the dish reflects do not fall upon the reading head.

The first light source can be used in combination with a second light source, or each one of them independently, according to the needs of each type of culture.

Besides, the invention is complemented by including some means for housing a plurality of dishes in an orderly fashion, so that the dishes are removed, placed in the camber and returned to the structure, one by one, to make the automatic count of the bacterial colonies; effecting the automatic introduction of the same.

The means for housing the dishes in an orderly fashion are defined by a preferably hexagonal base body, inside of which and in correspondence with the sides thereof some turrets defined by a plurality of horizontal compartments separated from each other, in which the dishes that remain slightly separated are placed, have been provided for.

The top base of the body is defined by two half moons that are fastened to a center by means of a nut. The sides of said half moons, and in correspondence with the center area of the hexagonal sides, have some vertical rods that face said hexagonal base, in such a way that the structure can be transported without the dishes falling, thus said structure can be used to place it with the dishes, inside the oven in which the reproduction of the bacteria is facilitated, whereby as the dishes are not contacting each other, the thermal balance can be attained; a circumstance that does not normally take place, and that favors the fact of a homogeneous distribution of temperature.

Besides, removal of the structure from inside the oven is permitted, the oven being placed near the contrast chamber to permit automatic introduction of the different dishes.

The top base of the structure has to be removed before carrying out the process of automatic introduction of the dishes inside the contrast chamber.

The bottom base of the structure interlocks with a motor that permits the rotation of the entire structure.

The hexagonal base of this structure is provided with a series of holes, through which it is possible for a worm that is driven by a motor to move, so that the lifting of each one of the turrets is furnished, whereby each and every one of the different dishes are positioned in the opening of the contrast chamber.

Besides, close to the contrast chamber there is a motor that controls an arm by means of which the chosen dish is removed, placing it inside the reflection chambers, and centering it in the same, in order to subsequently effect the count of the bacterial colonies and afterwards put the dish in the suitable place in the turret, and so on with each one of the different dishes.

Another feature of the invention consists of the bottom base of the contrast chamber being defined by a white opaque surface that enhances the reflection of light and diffusion thereof in the inside of the dish.

Therefore, by means of the invention the automatic introduction of a plurality of dishes is permitted, at the same time that the highlighting of the bacterial colonies is obtained to permit the automatic count of the same, by means of an automatic processor.

Another advantage of the invention consists of the fact that in the culture phase in which the dishes have remained in the oven, the thermal balance has been easily attained in the oven by the arrangement of the dishes.

Hereinafter to provide a better understanding of this specification and forming an integral part of the same, a series of figures in which the object of the invention has been represented in an illustrative and non-restrictive manner, has been attached hereto.

DESCRIPTION OF ONE OR SEVERAL EMBODIMENTS OF THE INVENTION

Figure 1:
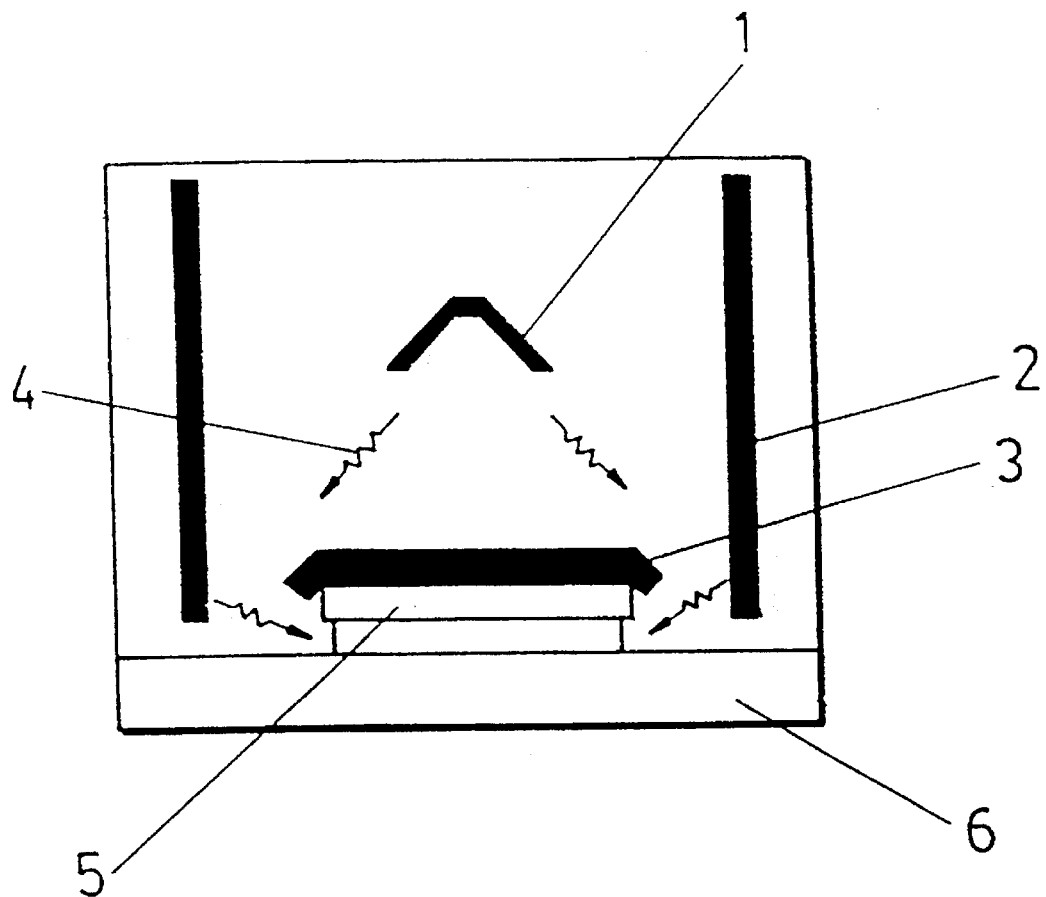
FIG. 1. It shows a schematic diagram of the contrast chamber in which the lighting up of the dish is done by reflecting light.
Figure 2:
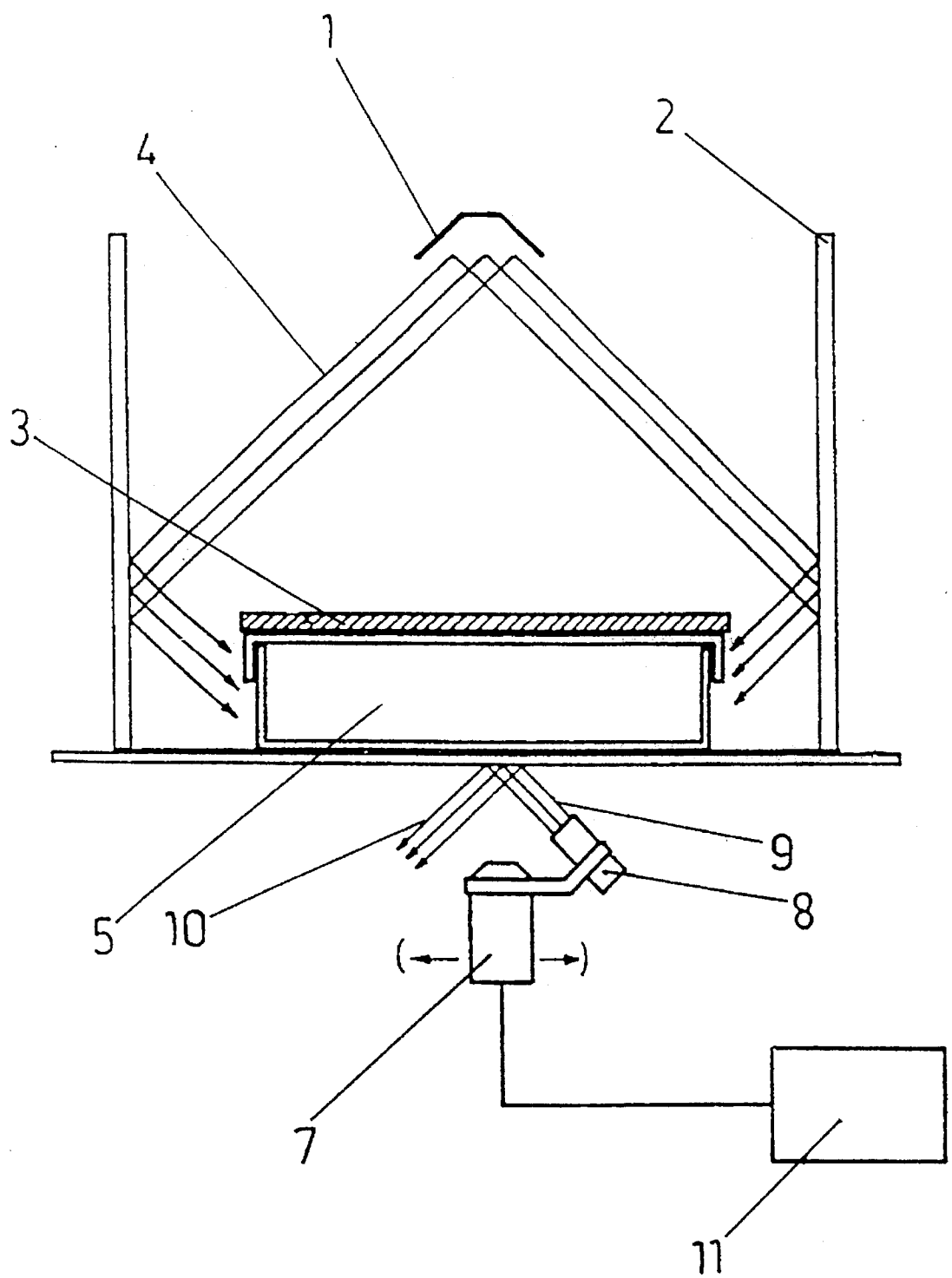
FIG. 2. It shows a schematic diagram equivalent to the previous figure, but with the addition of a second light source, that can operate independently or in combination with the previous one, improving the lighting conditions, and therefore the contrast obtained of the bacterial colonies with regard to the base in which the culture has been made.
Figure 3:
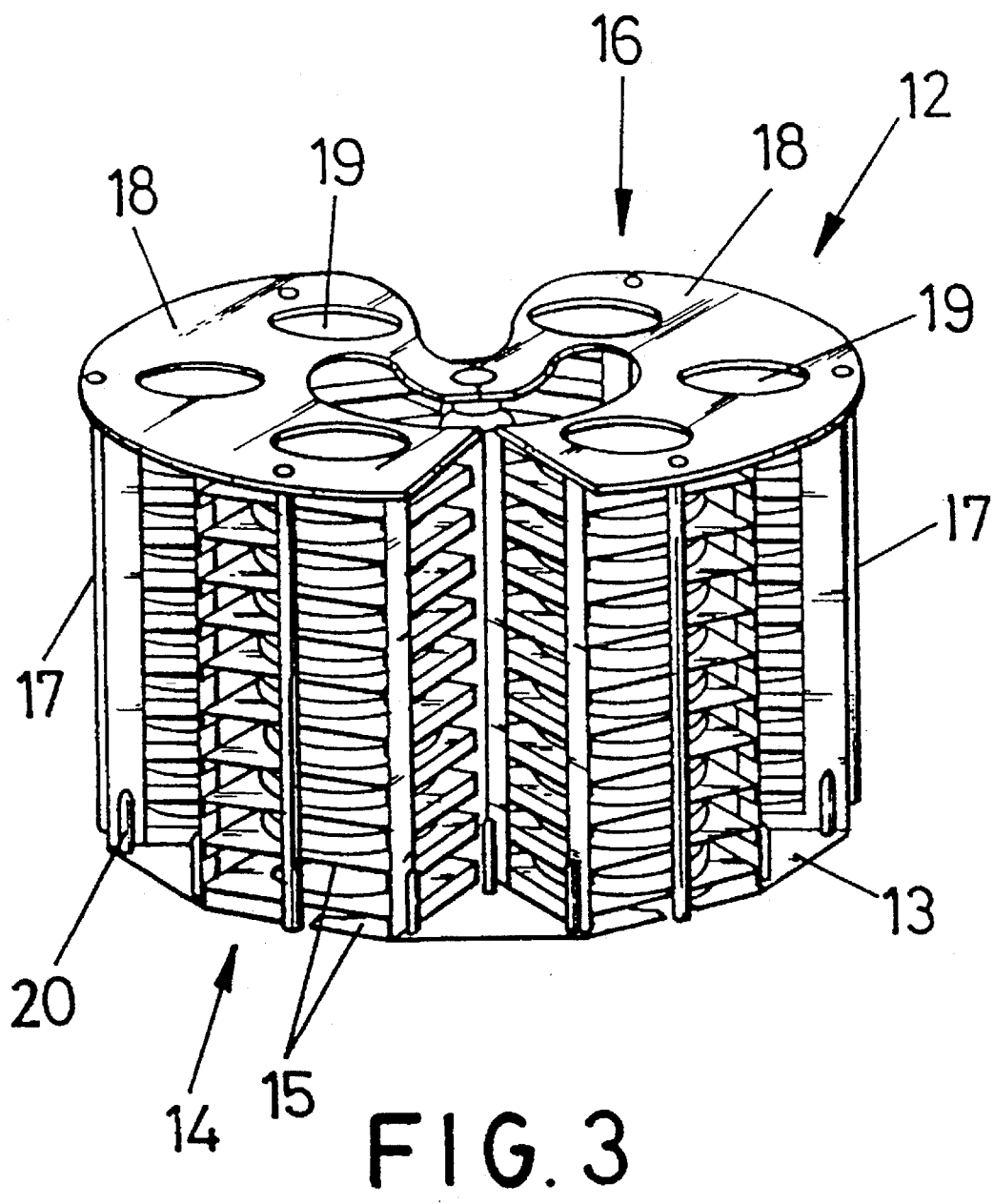
FIG. 3. It shows a perspective view of the structure that allows automatic introduction of a plurality of dishes inside the contrast chamber.

Hereinafter a description is made of the invention based on the above cited figures.

Conventionally use of dishes (5) is known to make bacterial cultures for the purpose of determining the number and type of bacteria present in food, a pharmaceutical product, etc. These dishes are known as Petri dishes.

Now then, the bacterial culture is made in dishes (5) in which a base product that consists of a gelled agaragar solution that constitutes the food for the bacteria is placed, upon which an extract of the product to be analyzed is placed.

Subsequently the dish is placed in an oven to enhance the reproduction of the bacteria, creating different colonies from each microorganism present in the extract.

The problem that is posed afterwards, consists of making the count of colonies created to establish the amount of bacteria present in the analyzed product.

Conventionally there are some systems for carrying out the count, which have the problems already described in the section corresponding to the background of the invention.

All those problems are solved by the present invention for which purpose it includes a reflection tube (2) inside of which a lamp (1) that gives off light (4) that is reflected on the inside walls of the reflection tube is housed.

Inside the reflection tube (2) the dish (5) is introduced automatically or manually. The dish (5) remains covered by an opaque cover (3) in such a way that when the lamp (1) is turned on, the lamp indirectly lights up the dish (5) on all sides. This effect is produced by the reflection of the light (4) on the inside walls of the reflection tube (2.)

The light is transmitted through the base product in which the culture is made, in such a way that the culture is completely lighted up whereby the bacterial colonies that have grown upon making the culture, remain highlighted upon the dark bottom.

The pickup of the image obtained of the culture is done by means of a reading head (7) that moves underneath the dish (5.)

The reading head (7) can be comprised of a scanner or other device or optical camera that permits the reading and transmission of the image obtained of the dish, to a computer or automatic processor (11) to be processed.

The image obtained can be represented on a screen (26) to likewise facilitate the fact of verifying the count of the bacterial colonies grown in the base product.

The lateral lighting of the dish can be done directly, for which purpose one or more lamps are placed lateral to the dish (5), effecting the contrast by direct lighting.

In this way, whether the lighting of the dish (5) is direct or indirect, visual or automatic pickup is permitted without errors, of the bacterial colonies. These described devices have the problem that if the number of colonies that appear in the culture is high, the central area of the dish is not adequately lighted up.

This problem can be overcome by means of including a second incandescent light source (8), transmitted preferably by optical fiber, that is fixed and moves with the reading head (7) and that gives off light rays (9) with a certain slant with regard to the base of the dish (5), so that the reflected rays (10) cannot fall on the reading head (7), since this circumstance would adversely affect the quality of the image obtained by the head (7.)

With the fixing of the light source on the reading head (7) an intense lighting up of the reading area is achieved, obtaining a high contrast of the image all over the dish (5.)

In this entire operation the cover of the dish is kept closed, circumstance that is not conventionally the case, just as it has been commented on above.

The dark opaque disk (3) is kept covering over the dish to highlight the contrast.

The reading head (7) is connected to an automatic processor, just as it has been commented on above, but with the exception that this connection can be done through an electronic circuit that permits the memorization of the image obtained for the subsequent processing and recording of the number of colonies in a totally automatic way, or visually by means of a screen (26.)

With the introduction of this second light source (8), the dish can receive lateral lighting by means of a light source (1) just as it has been described above, or by means of a second light source (8), both of which may operate simultaneously or independently, in terms of the type of culture to be examined.

Besides, the contrast chamber is capable of being blocked on its bottom surface by a opaque white surface (6) that enhances the diffusion of the light inside the dish, facilitating the lighting of the same through the bottom base thereof, using a single light source (1.)

Just as it was commented on above, the introduction into the contrast chamber of each one of the dishes is done automatically, for which purpose the invention has a structure like a basket (12) defined by a body whose bottom base (13) is preferably hexagonal and inside of which and in correspondence with each one of the sides some turrets (14) defined by a plurality of horizontal compartments (15) separated from each other in which the dishes (5) that remain slightly separated have been provided for.

The top base (16) of the body is materialized by two sorts of half moons or crescents (18) that are fastened to a center handle (25) by means of a nut. The sides of the half moons (18), and in correspondence with the center area of the hexagonal sides, have some vertical rods (17) that face the hexagonal base (13), so that the structure can be transported without the dishes falling out from the inside of the same; thus the structure can be used to place the dishes in the oven in which the reproduction of the bacteria is facilitated, whereby as the dishes do not contact each other, the thermal balance is attained, a circumstance that is not conventionally achieved.

Besides, removal of the structure from inside the oven is permitted, the oven being placed near the contrast chamber, to permit the count of the bacterial colonies produced in each one of the dishes (5.)

To facilitate the automatic introduction inside the contrast chamber, the structure (12) interlocks by its bottom base (13) with a motor (21) that permits rotation of the entire structure (12.)

At this point, it should be emphasized, that in order to carry out the automatic introduction of the dishes (5), it is necessary to remove the top base (16), turning the nut that fastens the two half moons (18), situation in which the turrets (14) can undergo vertical movement, as it will be stated hereinafter.

Figure 4A:
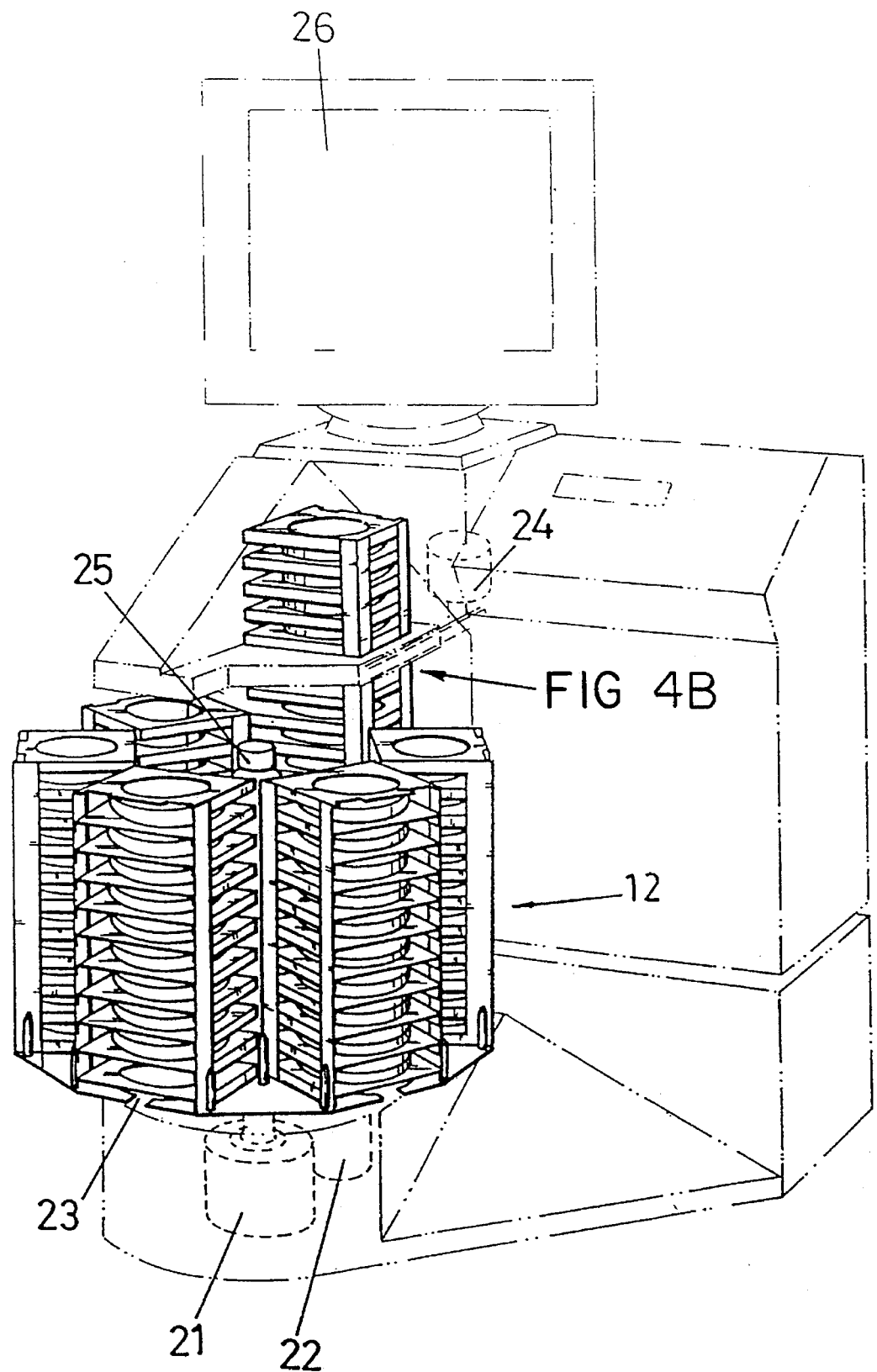
FIG. 4. It shows a perspective view of the arrangement of the structure, represented in the previous figure, with regard to the contrast chamber that is included in a frame that houses the processor and the different elements of the invention, in order to carry out the automatic reading of a plurality of dishes.
Figure 4B:
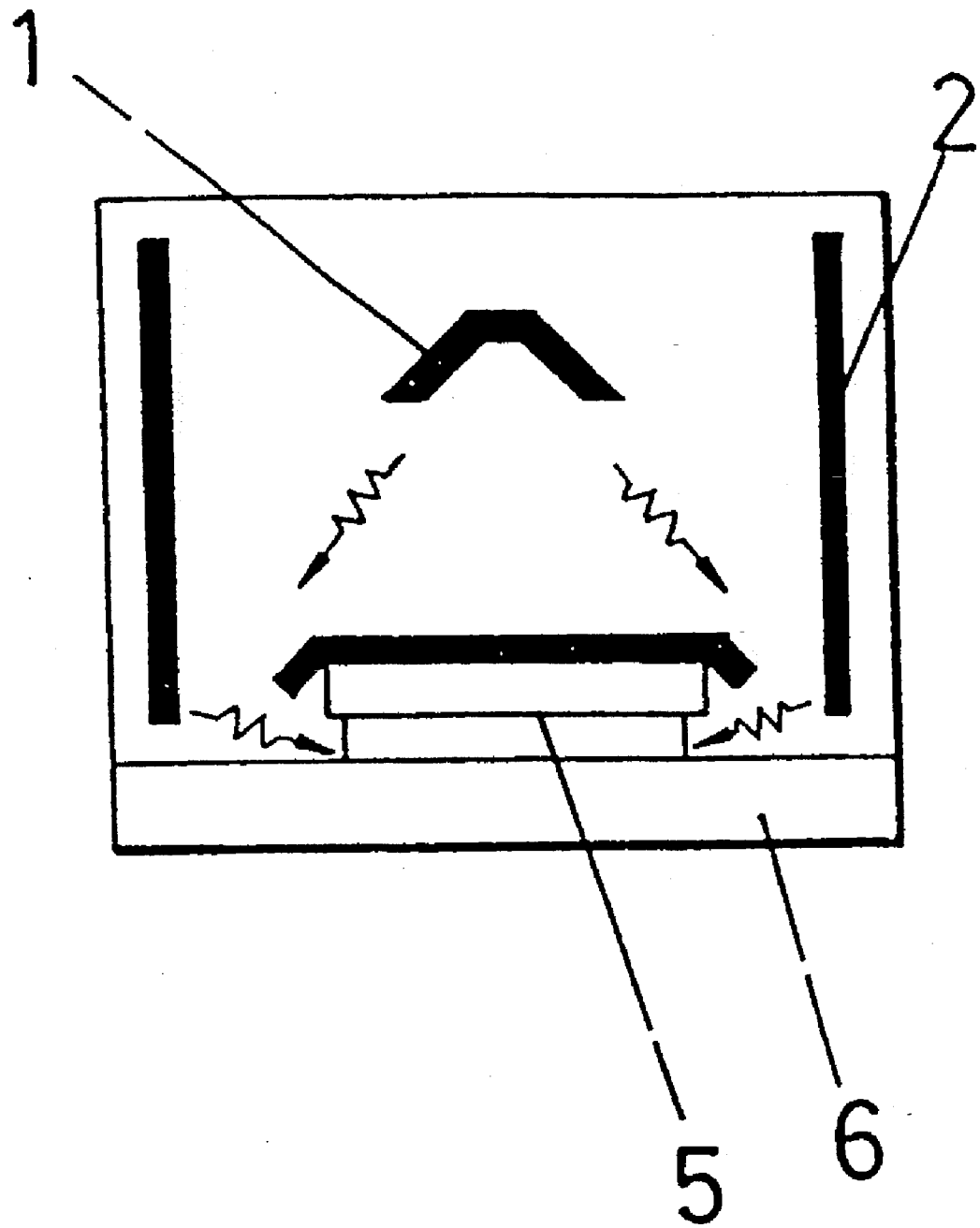

The bottom base (13) is provided with a plurality of holes (23), through which it is possible for a worm that is driven by a motor (22) to move, so that the lifting of each one of the turrets (14) is permitted, whereby each and every one of the different dishes (5) are positioned, in the opening of the contrast chamber (FIG. 4.)

Besides, close to the contrast chamber there is a motor (24) that interlocks by means of a rack with an arm by means of which the chosen dish is removed, by operation of the motors (21) and (22), placing it inside the chamber and centering it inside the same, in order to subsequently effect the count of the bacterial colonies and afterwards place the dish in the suitable place in the turret (14), and so on with each one of the different dishes.

Reference (19) indicates some holes made in the half moons (18) that constitute the top base (16), through which the dishes (5) that remain placed in the top part of each one of the turrets (14) are viewed.

Reference (20) represents some stops whose purpose consists of defining some turret (14) centering means.

All the elements that comprise the invention remain included inside a frame, represented by some dash lines in FIG. 4, whose structure represents a possible embodiment.

Therefore, by means of the invention a structure that facilitates the incubation stage to facilitate the growth of the bacterial colonies is provided, at the same time that it constitutes a means to allow automatic introduction of the dishes and the making of the count, which is also automatic, of the different colonies produced in the culture.

I claim:

1. A device including a contrast chamber to spotlight optically bacterial colonies grown in a plurality of dishes which contains a culture medium in which the bacterial colonies are disposed to permit an automatic count of said colonies by means of an automatic processing means and a reading head connected to said automatic processing means, said device comprising:

a contrast chamber including a first supporting means for supporting a dish;

second supporting means for supporting said reading head in a position under said dish, said reading head being separated from said dish by a transparent member, said reading head being positioned and movable in a horizontal plane with respect to said dish;

illumination means for illuminating said dish supported in the contrast chamber, said illumination means emitting light rays disposed at an angle with respect to the horizontal plane; said angle being other than 90°; and a dark opaque disk element being disposed above said dish that is supported in the contrast chamber, said disk element being disposed in a horizonal plane.

2. A device according to claim 1, wherein the contrast chamber includes a plurality of vertical walls, said plurality of vertical walls being reflective.

3. A device according to claim 2, wherein the illumination means includes a top light source positioned vertically above the disk element such that the disk element obstructs the top area of said dish supported by the first supporting means in the contract chamber from light rays emitting from said top light source such that said dish will be illuminated sideways by light reflected from the inside surfaces of the vertical walls.

4. A device to claim 1, wherein the illumination means includes a bottom light source positioned vertically below the disk element such that said illumination means illuminates said dish supported by the first supporting means in the contrast chamber, from below, said bottom light source being positioned with respect to the reading head such that rays emitting from the bottom light source and reflected by a flat bottom of said dish supported by the first supporting means will not be redirected upon the reading head.

5. A device according to claim 4, wherein the illumination means includes a top light source positioned vertically above the disk element such that the disk element obstructs the top area of said dish supported by the first supporting means in the contract chamber from light rays emitting from said top light source such that said dish will be illuminated sideways by light reflected from the inside surfaces of the vertical walls.

6. A device according to claim 5, wherein the top light source includes a lamp and the bottom light includes a source for incandescent light and an optical fibre for transmitting said incandescent light, and the device further includes means for activating said top light sources and said bottom light source.

7. A device according to claim 1, wherein the illumination means include a plurality of light sources disposed horizontally and sideways with respect to said dish supported by the first supporting means.

8. A device according to claim 7, wherein the illumination means includes a bottom light source positioned vertically below the disk element such that said illumination means illuminates said dish supported by the first supporting means in the contrast chamber, from below said bottom light source being positioned with respect to the reading head such that rays emitting from the bottom light source and reflected by a flat bottom of said dish supported by the first supporting means will not be redirected upon the reading head.

9. A device according to claim 8, wherein the bottom light source includes a source for incandescent light and an optical fibre for transmitting said incandescent light, and the device further includes means for activating the plurality of lamps and said bottom light source.

10. A device according to claim 1, wherein the device further includes a housing means for housing said plurality of dishes and removing means for removing dishes from said housing means.

11. A device according to claim 10, wherein said housing means include a basket-like structure with a hexagonal bottom base supporting, in correspondence with the sides thereof, a predetermined number of turrets, each of said turrets comprising a plurality of horizontal compartments in which dishes can be placed so that the dishes are slightly separated from each other, thereby achieving that each dish more easily reaches a corresponding thermal balance when the housing means is placed into an oven, and thereby also facilitating removal and return of the dishes from and to the turrets.

12. A device according to claim 11, wherein the housing means include a top base comprising two top base portions, each of said top base portions being crescent shaped, said top base portions being fastened to a central handle;

the housing means further includes a number of vertical rods which protrude downwardly from the top base portions and whose distal ends face a peripheral portion of the bottom base in positions that are located centrally with respect to sides of the turrets so that the dishes are retained in the compartments.

13. A device according to claim 11, wherein the bottom base interlocks with a first motor for rotating the housing means; and wherein the turrets are provided with holes through which a worm activated by a second motor can move;

a third motor interlocking, by a rack and an arm, to manipulate a position of one of said dishes.

14. A device according to claim 13, wherein the contrast chamber includes a bottom base with an opaque white surface that obstructs said contrast chamber and that constitutes a support means for a dish, said opaque white surface improving luminosity by facilitating scattering of light through the inside of said dish when the top light source is the only illumination means that is used.

15. A device according to claim 1, wherein the automatic processing means is connected to a screen to permit visual verification of the count of the bacterial colonies.

* * * * *